United States Patent [19]
Ashby et al.

[11] Patent Number: 5,911,723
[45] Date of Patent: Jun. 15, 1999

[54] SURGICAL APPARATUS

[75] Inventors: Alan Ashby, Everton; Mark A. Cowling, Devon, both of United Kingdom

[73] Assignee: Howmedice International Inc., Shannon, Ireland

[21] Appl. No.: 08/864,168

[22] Filed: May 28, 1997

[30] Foreign Application Priority Data

May 28, 1996 [GB] United Kingdom ................ 9611074.7

[51] Int. Cl.⁶ .................................................. A61B 17/56
[52] U.S. Cl. ............................................... 606/88; 606/90
[58] Field of Search ................... 606/90, 88, 89, 606/87, 86, 102

[56] References Cited

U.S. PATENT DOCUMENTS

| | | |
|---|---|---|
| 4,501,266 | 2/1985 | McDaniel . |
| 4,566,448 | 1/1986 | Rohr, Jr. . |
| 4,646,729 | 3/1987 | Kenna et al. . |
| 4,653,488 | 3/1987 | Kenna et al. . |
| 5,116,338 | 5/1992 | Poggie et al. . |
| 5,213,112 | 5/1993 | Niwa et al. . |
| 5,468,244 | 11/1995 | Attfield et al. . |
| 5,514,143 | 5/1996 | Bonutti et al. . |
| 5,540,696 | 7/1996 | Booth, Jr. et al. ................ 606/88 |
| 5,669,914 | 9/1997 | Eckhoff ............................. 606/88 |

FOREIGN PATENT DOCUMENTS

| | | |
|---|---|---|
| 2648699 | 12/1990 | France . |
| 2261604A | 5/1993 | United Kingdom . |

*Primary Examiner*—Guy V. Tucker
*Attorney, Agent, or Firm*—Peter C. Richardson; Lawrence C. Akers; Raymond W. Augustin

[57] ABSTRACT

A surgical tensioning apparatus has a base, first and second bone tissue engaging elements mounted on the base and being displaceable toward and away from each other. One of the tissue engaging elements being adapted to be oriented by the tissue engaged thereby. A guide element is provided which is adjustable in relation to the base and one of the tissue engaging elements for positioning first location element to locate a cutting guide provided with cooperating second location element onto the bone to be resectioned.

15 Claims, 15 Drawing Sheets

FIG-2
2 ANTERIOR FEMUR
4 POSTERIOR FEMUR
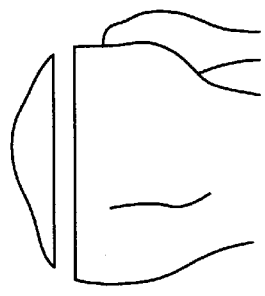
6 TRANSVERSE PROXIMAL TIBIA
1 DISTAL FEMUR
3 ANTERIOR CHAMFER
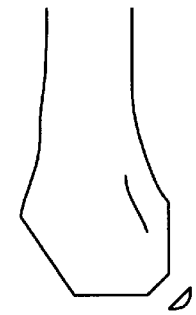
5 POSTERIOR CHAMFER

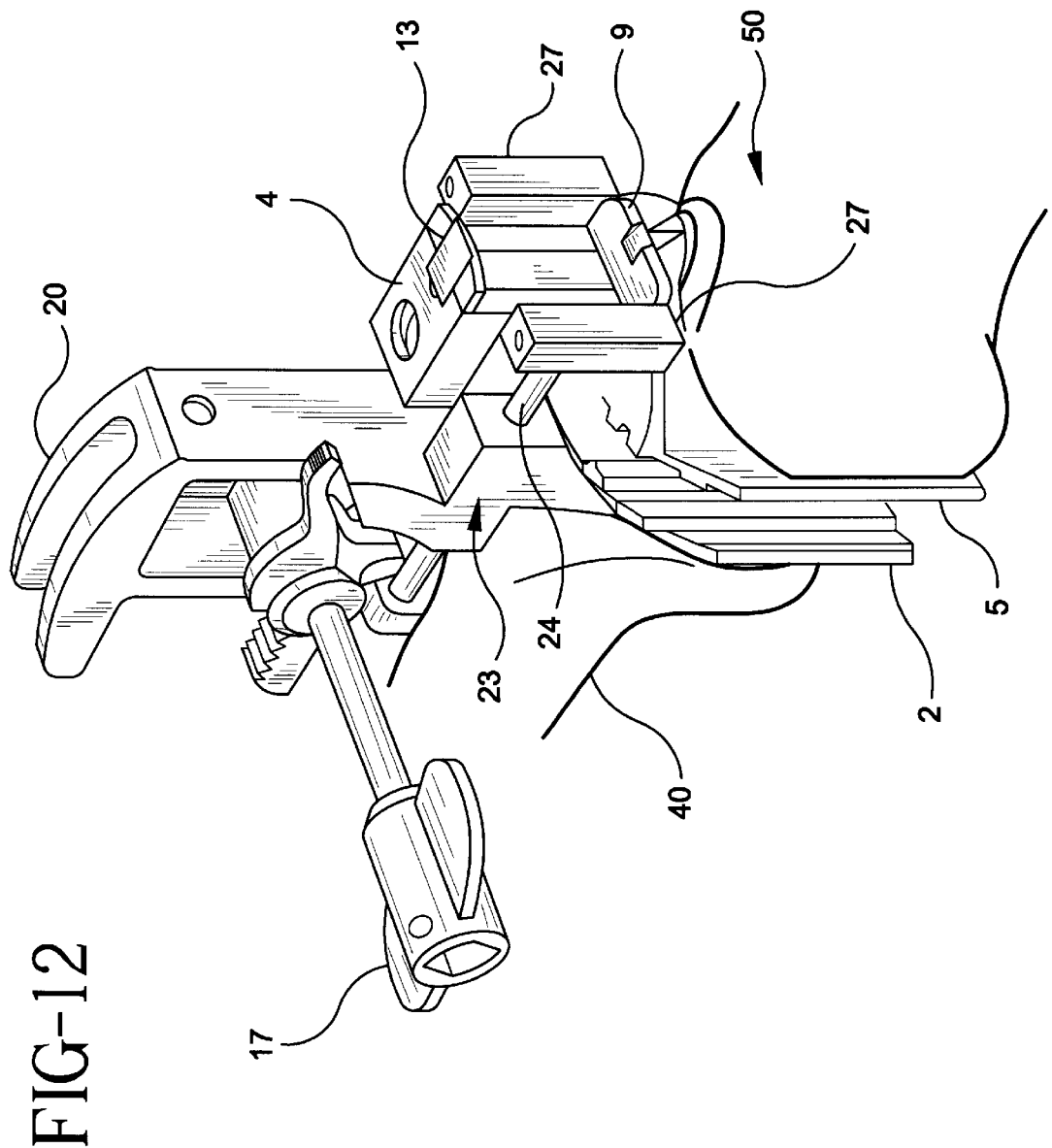

SURGICAL APPARATUS

BACKGROUND OF THE INVENTION

1. Field of the Invention

This invention relates to surgical ligament tensioning apparatus which is particularly, although not exclusively, applicable for use in surgery of the knee and especially total knee arthroplasty.

2. Description of the Prior Art

The surgical goals of knee arthroplasty are relief of pain and restoration of functional mobility of the knee. The key factors in achieving these goals include the maintenance of correct prosthetic alignment, fixation and articulation.

The majority of knees presented for treatment with total knee arthroplasty suffer a ligamentous imbalance which can lead to a decreased range of motion, instability of the implant and increased polyethylene wear if such a material is used in the prosthesis.

During such operations it is therefore necessary to eliminate the passive deforming forces around the knee associated with soft tissue imbalance at the time of surgery. This is achieved by graduated soft tissue release of the contracted tissues around the knee. In order to carry out this technique successfully, the surgeon has to ensure that the knee is symmetrically balanced both medio laterally and between flexion and extension. In the past, this has been done by eye judgment which is difficult, since, if after surgery the knee is imbalanced, then failure of the prosthesis can result.

U.S. Pat. No. 5,468,244 shows a surgical apparatus for use in a tensor based technique for knee surgery which employs first and second tissue engaging means displaceable towards and away from each other. One of the tissue engaging means is arranged to be oriented by the tissue engaged and measuring means are provided to measure displacement between the tissue engaging means and also measure the rotation of the appropriate tissue engaging means so that the imbalance can be corrected by eliminating the necessary soft tissue to ensure that the ligamentous imbalance is corrected prior to the fitting of the prosthesis.

The present invention is intended to provide apparatus which can be used in a tensor based technique and which addresses the critical issues of correction positioning, restoration of the joint's functional mobility and the long term survivorship of the knee prosthesis through improved alignment and greater stability and relies upon an improved construction of the surgical apparatus shown in U.S. Pat. No. 5,468,244.

SUMMARY OF THE INVENTION

According to the present invention, surgical apparatus comprises a base, first and second bone tissue engaging means mounted on said base and being displaceable towards and away from each other, one of said tissue engaging means being adapted to be orientated by the tissue engaged thereby, and guide means adjustable in relation to said base and one of said tissue engaging means for positioning first location means to locate a cutting guide provided with cooperating second location means onto a bone to be resectioned.

Thus, when the apparatus is used in joint replacement surgery, the tissue engaged by the first and second engaging means is bone tissue.

The guide means can include a guide bore, and this can be dimensioned to receive said first location means which is an elongate element to be inserted into said bone.

The elongate element may be a drill, screw, nail, rod or pin.

With this arrangement, the second location means can be provided by a location opening in said cutting guide.

In an alternative construction the first location means can be an opening in said bone which can be formed by an elongate forming means guided through said guide bore.

The second location means in this construction is provided by an abutment on said cutting guide and which is dimensioned to locate in said opening in the bone.

The cutting guide can be provided with additional openings to receive attachment elements to further locate it on the bone.

Preferably the tissue engaging means each include a tissue engaging surface, each of said tissue engaging surfaces being arranged so that it faces away from the other.

The drill guide can be arranged to move in relation to the base in accordance with movement of one of the tissue engaging surfaces.

With this arrangement the guide can be carried by the tissue engagement means.

Alternatively, the guide can be movably located on the base and can be arranged to be moved in only one direction by the tissue engaging means.

In a preferred construction, the guide is carried by a friction locking means which can be arranged to be releasable.

For dealing with knee arthroplasty two guides can be included, arranged in spaced apart relationship in relation to one of said tissue engaging means.

The first tissue engaging means can be located in fixed relationship to the base and said second tissue engagement means can move in relation to said base, said second tissue engaging means comprising a movable head carrying a tissue engaging element provided with a tissue engaging surface, said guide means being carried on or moved by engaging said movable head.

The guide means can engage the movable head and be carried on a support movably mounted on the base.

The second tissue engaging means can be adapted to be oriented by the tissue engaged thereby, the movement being rotatable.

Measuring means may be provided to measure the degree of deflection of the said second tissue engaging surface away from a position of parallelism with the first tissue engaging surface when said first and second tissue engaging means engage the tissue.

The apparatus may also include means to displace the tissue engaging means away from each other which may include a geared drive, for example, a rack and pinion assembly.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 2 is a diagrammatic illustration showing the positioning of the five femoral bone cuts made for the application of a knee prosthesis;

FIG. 12 shows the apparatus being used for ligament tensing in extension;

DESCRIPTION OF THE PREFERRED EMBODIMENT

When preparing a bone to receive a prosthesis, anatomic references are taken from the natural bone. Thus, when fitting a knee prosthesis anatomic references are taken from the femoral medullary canal, center of the femoral head, center of the knee joint and center of the ankle.

Figure 1:
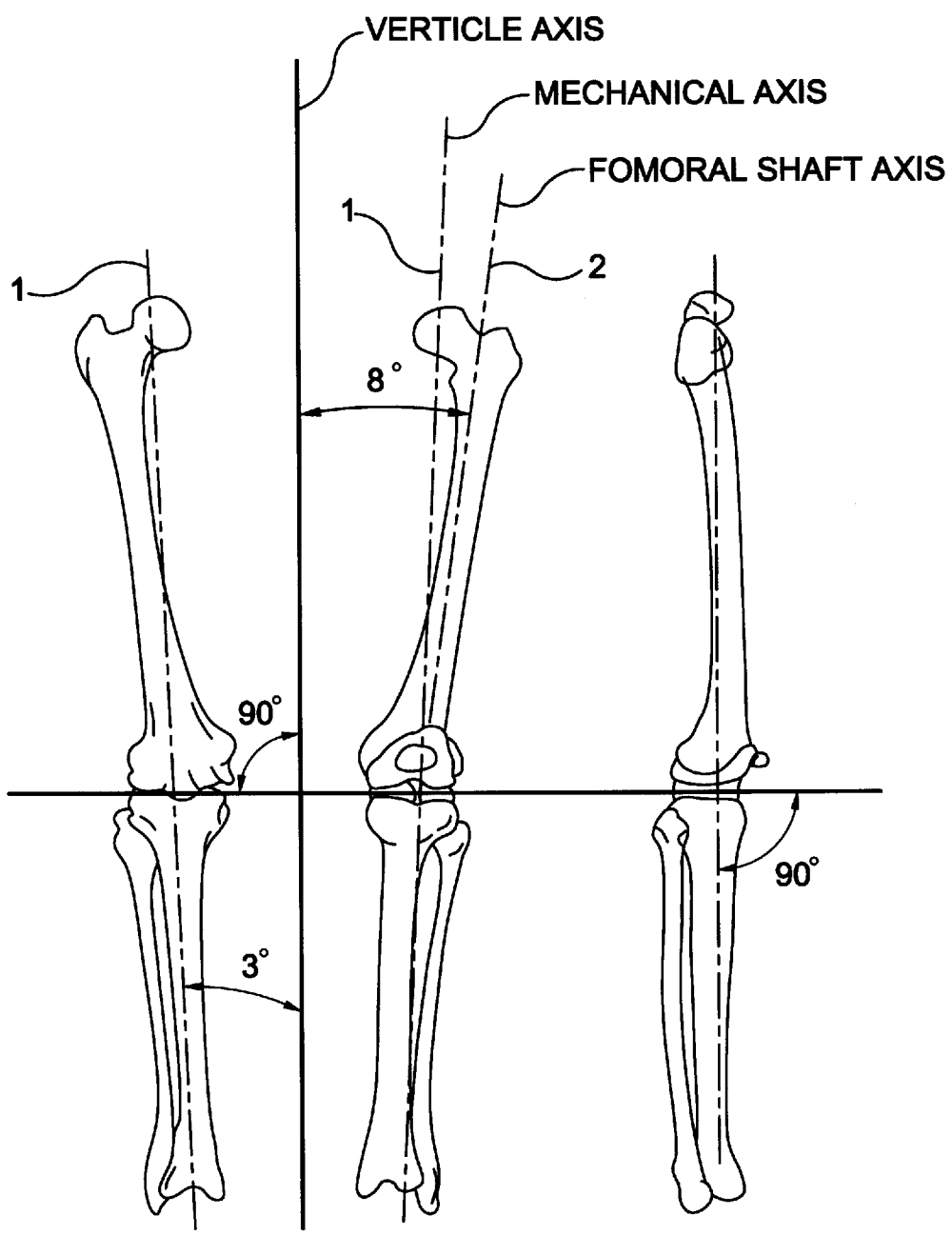
FIG. 1 is a diagrammatic representation of the configuration of the bones of a human leg and knee joint, the representation on the left showing the natural knee and the two views on the right showing such a configuration fitted with a prosthetic knee construction.
Figure 3:
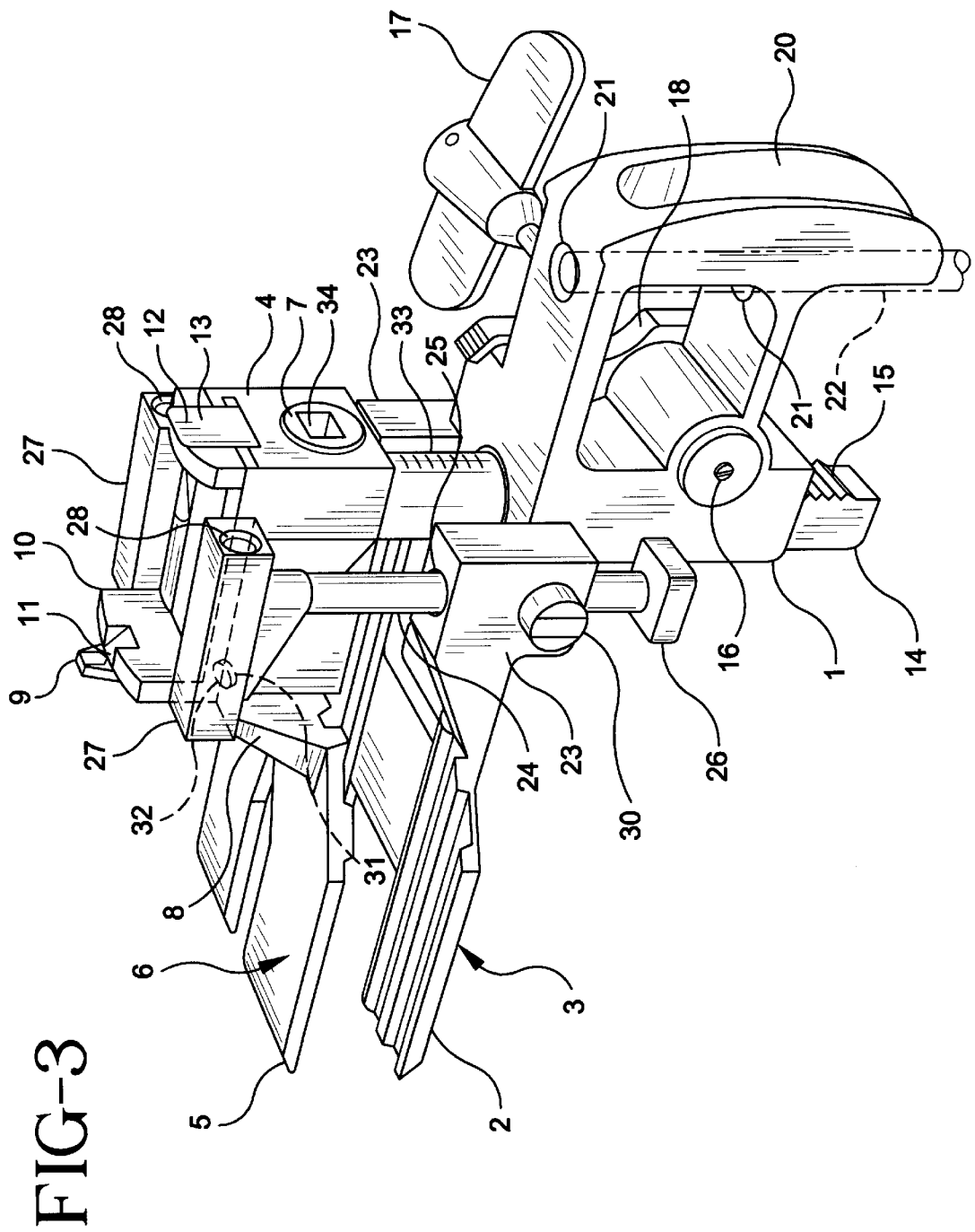
FIG. 3 is an isometric view showing the surgical apparatus according to the invention.

On a normal knee, as shown on the left hand side of FIG. 1, the mechanical axis is defined by a straight line joining the centers of the hip and ankle which passes slightly medially to the center of the knee and which is indicated by broken line 1. The orientation of the bones when supplied with a knee prosthesis is shown on the righthand side of FIG. 1. Since a femoral shaft 2 forms an angle with the mechanical axis 1 and this angle varies between patients, 4°, 6° and 8°, intramedullary (I-M) alignment rods are provided (not shown). Overall operative alignment is best seen on a full length X-ray with the patient in a single leg stance. Where this is not possible, dual leg stance is acceptable where the centers of the hip, knee and ankle are shown on a single film. In contrast to the convention anterior referencing (A-R) and posterior referencing (P-R) techniques the aim of the technique employing the present invention is to position the femoral component so that the ligament tension in both flexion and extension is balanced.

FIG. 2 shows the five femoral cuts required and the apparatus according to the present invention provides alignment and positioning of the five femoral bone cuts relative to I-M or extramedullary (E-M) references. It is intended that the prosthetic components are positioned at 90° to the mechanical axis in the coronal plane and sagittal plane.

The present invention incorporates apparatus for use with a system for equally spacing and tensing the knee in flexion and extension and for positioning the femoral resection guides. From the positioning of the cutting guide, the ligament tension of the knee in flexion and extension is controlled.

Medio lateral soft tissue imbalance is quantified by the level of angular displacement in the joint when the soft tissues draw the joint into its equilibrium position. The apparatus according to the invention helps to resolve the imbalance in the knee by enabling accurate intra-operative measurement of angular displacement in the coronal plane during ligament release. The ligaments of the knee are release and/or repositioned in the attempt to balance the medial and lateral forces in the joint.

The apparatus according to the invention and which is for use in knee surgery comprises a base 1, a first tissue engaging means 2 which is located in fixed relationship to the base 1 and has a tissue engaging surface 3. A movable head 4 carries a second tissue engaging means 5 which has a tissue engaging surface 6. It will be seen that the tissue engaging surfaces 3 and 6 face away from each other.

The second tissue engaging means 5 is carried in the head 4 on a rotatable shaft 7, the rotatable axis of which is parallel with the tissue engaging surface 3. The tissue engaging surface 5 carries a plate 8 the upper end of which provides a pointer 9 which moves with the spindle 7 and with relation to an arc-shaped plate 10 provided with a scale 11 which indicates the degree of rotational movement relative to the head 4 and thus the tissue engaging surface 3. Lock means 12 are provided which include an upstanding tab 13 connected to a plate (not shown) which can operate against the plate 8 to alternatively lock the tissue engaging surface 6 in a first position in which it is parallel with the tissue engaging surface 3 or, when the tab 13 is moved back to a second position, allow the shaft 7 to rotate 5° in either direction, or to a third position in which the shaft 7 is free to rotate in either direction.

The head 4 is connected to the base 1 by a shaft 14 which carries the rack 15 of a rack and pinion geared drive. The pinion (not shown) is carried on a spindle 16 located in the base 1 and can be rotated by a key 17. A ratchet lever 18 acts on a ratchet wheel 19 (most clearly shown in FIG. 13). The construction is such that when the key 17 is operated in an anti-clockwise direction, the ratchet arrangement allows the spindle 17 to be rotated to engage the rack 15 and move the tissue engaging means 5 away from the tissue engaging means 2 so that they are displaceable away from each other. The ratchet prevents the key 17 from being operated in a clockwise direction to move the tissue engaging means 5 and 2 toward each other unless the ratchet lever 18 is released.

The base 1 is provided with a handle 20 which carries a pair of openings 21 to receive an E-M rod indicated by broken lines 22.

Carried on the base 1 are a pair of spaced apart guide members 23 which support a pair of guide shafts 24. Each guide shaft 24 extends through an opening 25 in its respective member 23 and they are connected together by a tie member 26. The opposite end of each guide shaft 24 carries guide means in the form of a drill guide block 27 with a guide bore formed by a drill guide opening 28 as in the construction shown the first location means to be used are elongate elements provided by drill bits. The longitudinal axis of each drill guide opening 28 is parallel with the tissue engaging surface 3. One of the shafts 24 is provided with a friction locking means in the form of a fine rack on its inner side (not shown) which is engaged by a resilient element located within the guide member 23. This resilient member is connected to a push button 30 so that it can be moved away from the rack to allow free movement of the interconnected shafts 24.

The wall of each drill guide 27 adjacent the head 4 is provided with an indentation 31 which can be engaged by a projecting pin 32 located on the side wall of the head. Thus, when the head 4 is moved away from the tissue engaging surface 3, the indentations 31 engage on the pins 32 and raise the drill guides in unison with the movement of the head 4. When the tissue engaging means 5 and 2 are displaced towards each other, the pins 32 can move down and evacuate the indentation 31, thus leaving the drill guides 27 in position, where they remain due to the friction locking means. The drill guides 27 can, however, also be moved downwards either by overriding the tissue locking means or by releasing them by operation of the button 30.

It will therefore be seen that the drill guides 27 move in relation to the base 1 in accordance with movement of the second tissue engaging surface 6 when the tissue engaging means are displaced away from each other.

In an alternate construction, the drill guides 27 can be fixed to the tissue engaging means 5 themselves.

The surface of the shaft 14, above the rack 15, is provided with graduations 33 to provide measuring means to measure the degree of deflection of the second tissue engaging surface 6 away from a position of parallelism with the first tissue engaging surface 3 when the first and second tissue engaging means are displaced apart.

The spindle 7 is provided with a square section opening 34 to receive a square guide provided on an intramedullary rod to be described hereunder. The key 17 locates in a suitably shaped opening in the spindle 16 so that it can be removed and/or can be replaced by a suitable torque wrench.

The operative technique which employs the apparatus described above first requires tibial resection. Thus, a tibial jig, of known kind, is used to make the tibial resection 0° A-P and 0° medio-lateral (M-L) planes. An opening into the I-M canal in the femur is made by drilling a hole slightly medial to the center of the intercondylar groove and aligned along the axis of the femur. Drilling should be to a depth of 20–30 mm, just sufficient to break through the hard bone. In the technique being described, the tibia is indicated by reference numeral 40 and the femur by reference numeral 50, the drilling in the femur being indicated by reference numeral 51 in FIGS. 4, 5, 13, 14 and 15.

Figure 4:
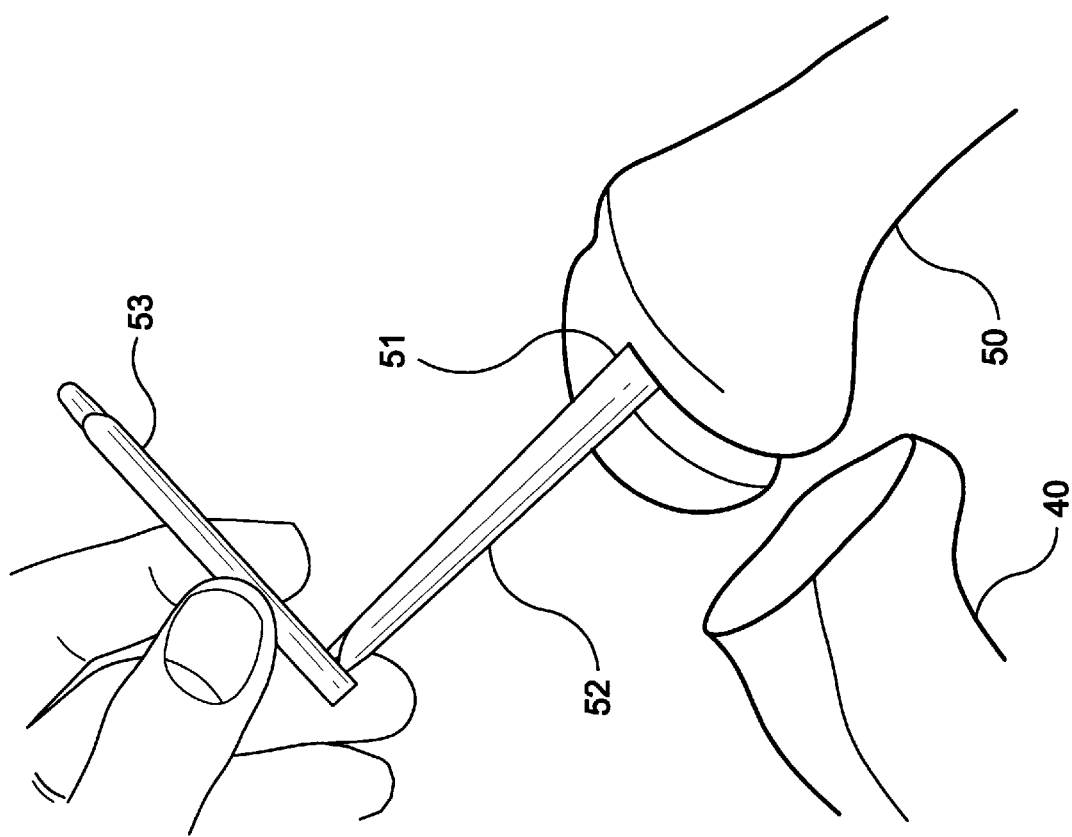
FIG. 4 is a diagrammatic illustration showing how an intramedullary rod can be fitted and provided with a guide.

Femoral I-M alignment is now carried out. The correct valgus orientation of the patient's femoral shaft should be determined preoperatively. I-M rods are available in 4°, 6° and 8° valgus angle. Selecting the correct angle of I-M rod 52, it is slowly inserted into the I-M canal through the opening 51 as indicated in FIG. 4.

For a further alignment check, or in cases where it is not possible to use an I-M rod, E-M alignment can be used. With this arrangement an E-M rod 22 is inserted through the openings 21 of the handle 20 of the apparatus and the leg is aligned with the mechanical axis.

The apparatus according to the present invention is now employed. The head 4 is moved so that the tissue engaging means 2 and 5 are together and the tissue engaging means 5 is locked in position by the tab 13 so that the tissue engaging surfaces 3 and 6 are parallel. The drill guides 27 are reset to the lowest position, that is they are pushed downwardly so that the recesses 31 locate on the pins 32 and it must be ensured that the tissue engaging surface 3 on the first tissue engaging means 2 is sitting flush on the cut proximal tibia 40.

Figure 5:
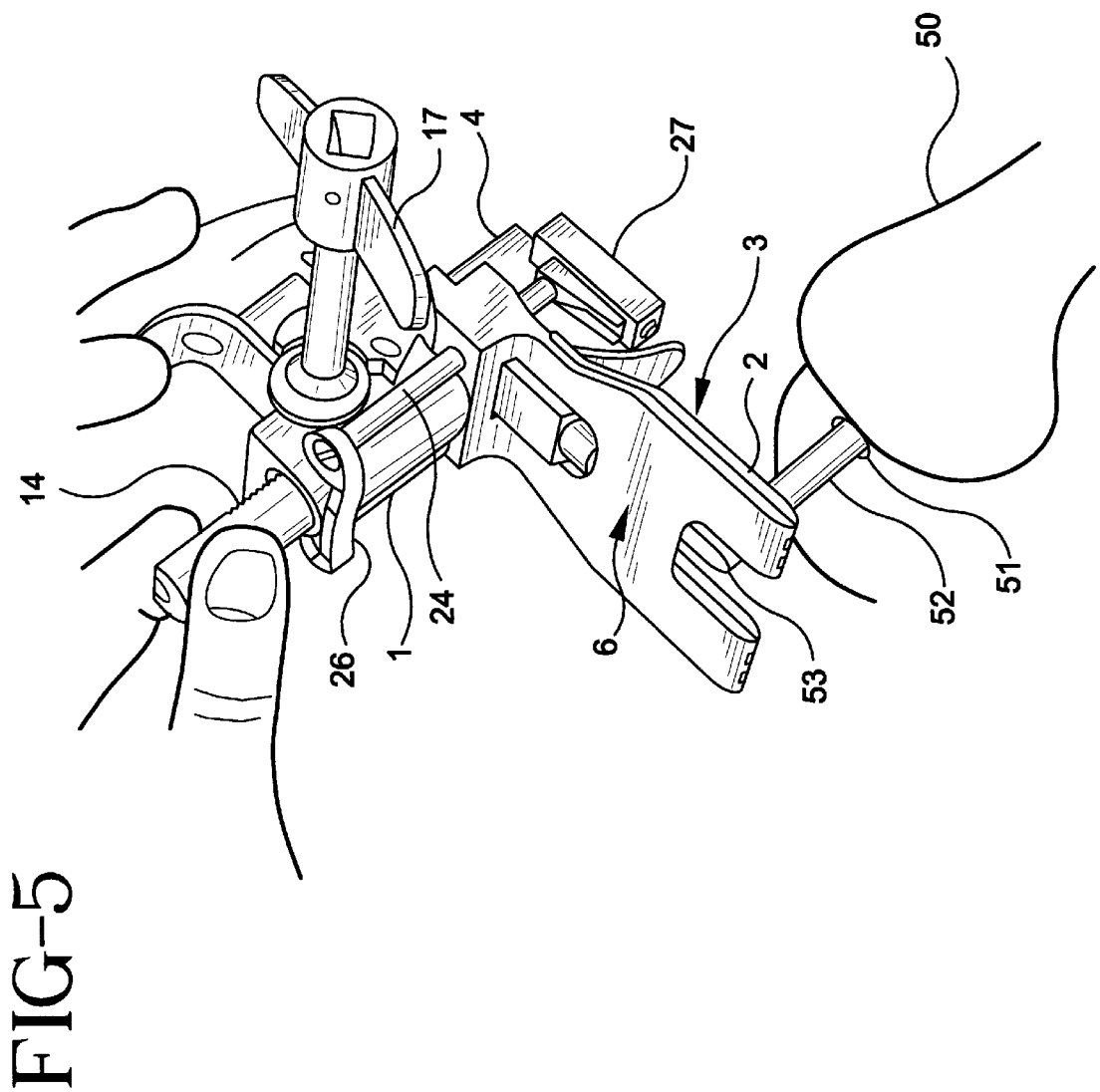
FIG. 5 is an isometric view showing the apparatus according to the invention being fitted onto the guide shown in FIG. 4.

The apparatus is assembled onto a square section I-M rod extension 53 by placing the rod into the square section opening 34 in the locked spindle 7, as shown in FIG. 5.

It is important that, when assembled, the jaws of the apparatus, as provided by the tissue engaging means 2 and 5 are pushed into the knee as far as possible and that the second jaw provided by the tissue engaging means 2 is in contact with the distal condyles.

Figure 6:
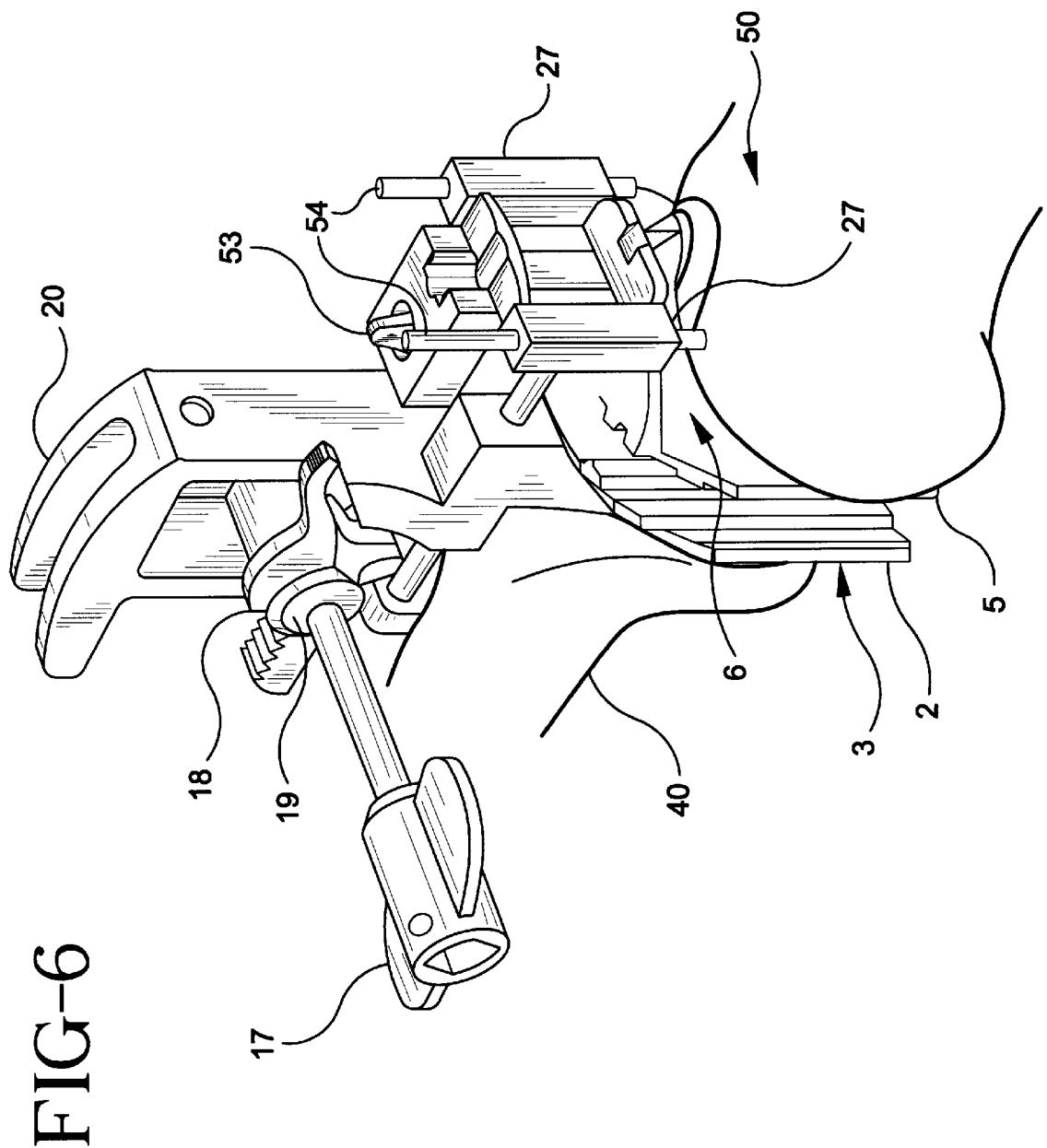
FIG. 6 is an isometric view showing the apparatus being aligned and for use in a femoral distal resection process.

With the knee in full extension, the apparatus is now aligned with the femur at the said valgus angle (4°, 6°, 8°) from the mechanical axis in the frontal plane and perpendicular in the sagittal plane. The jaws of the apparatus are distracted until contact is made by the surface 6 with the femoral condyle or condyles. A 3.2 mm drill 54 is now tapped or drilled through each drill guide 27 into the femur 50, as shown in FIG. 6 to act as first location means for a resection cutting guide.

It should be noted that a deficient condyle will not upset alignment.

The knee is now flexed and the apparatus is removed together with the I-M rod 53. It may be helpful to hammer the drill pins 54 and 55 flush with the drill guides and release the tension from the jaws by releasing the ratchet lock 18 and the rotation latch 13.

Figure 7:
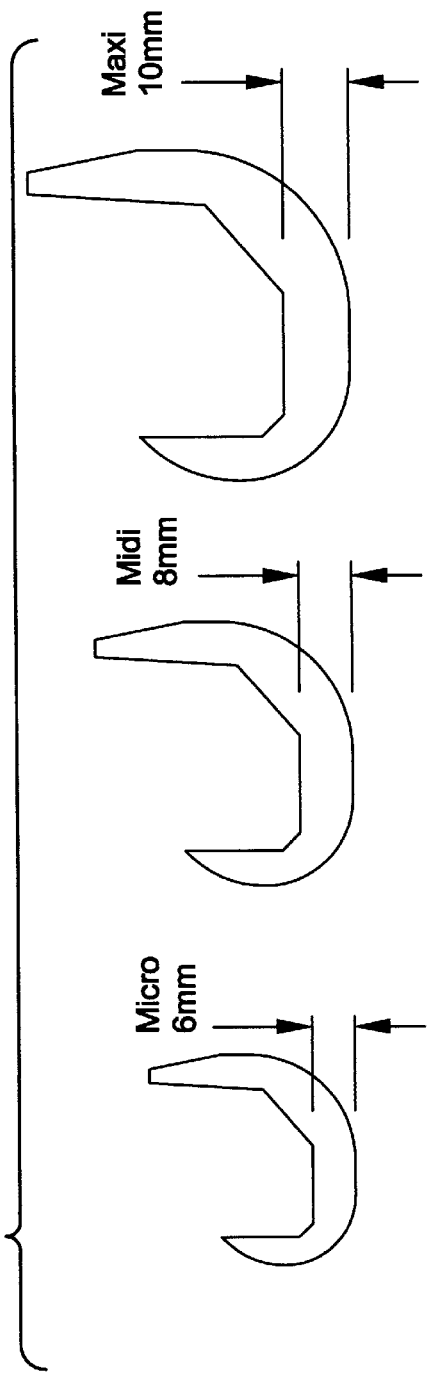
FIG. 7 is a diagrammatic illustration showing three sizes of femoral prosthesis which can be fitted.

FIG. 7 shows three sizes of femoral prosthesis which can be used, (micro/midi/maxi), and which require different cuts.

Figure 8:
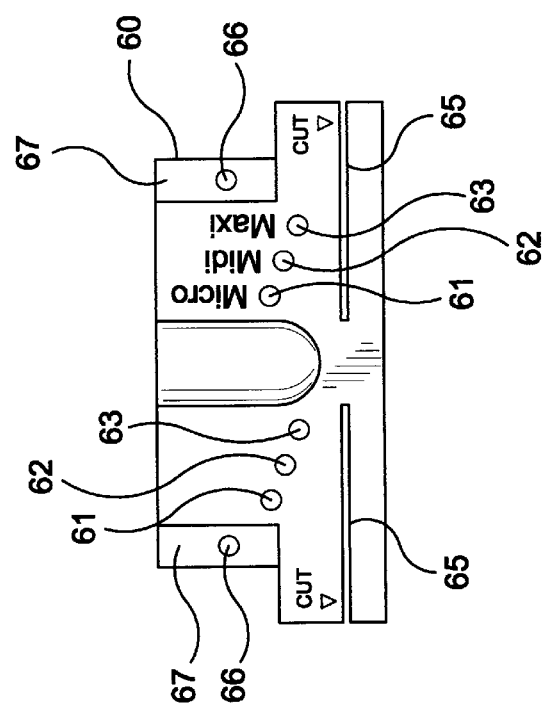
FIG. 8 is a plan view of a cutting guide for use with the apparatus.

The cutting guide 60 which is used is shown in FIG. 8 and is provided with second location means in the form of spaced apart location openings. The openings are in pairs which are indicated by reference numerals 61, 62 and 63 and are positioned to match the three sizes of femoral prosthesis.

Cutting slots 65 are also provided as are two additional openings 66 to receive further attachment elements in a manner to be described.

The correct sized cut (micro/midi/maxi) is now selected and the distal resection cutting guide is slid onto the drill pins 54 using the appropriate openings 61, 62 or 63 to locate on the drill pins. To further secure the resection guide 60, drills or fixing pins are employed through additional openings 66 provided in the resection guide on its angled sides 67.

Figure 9:
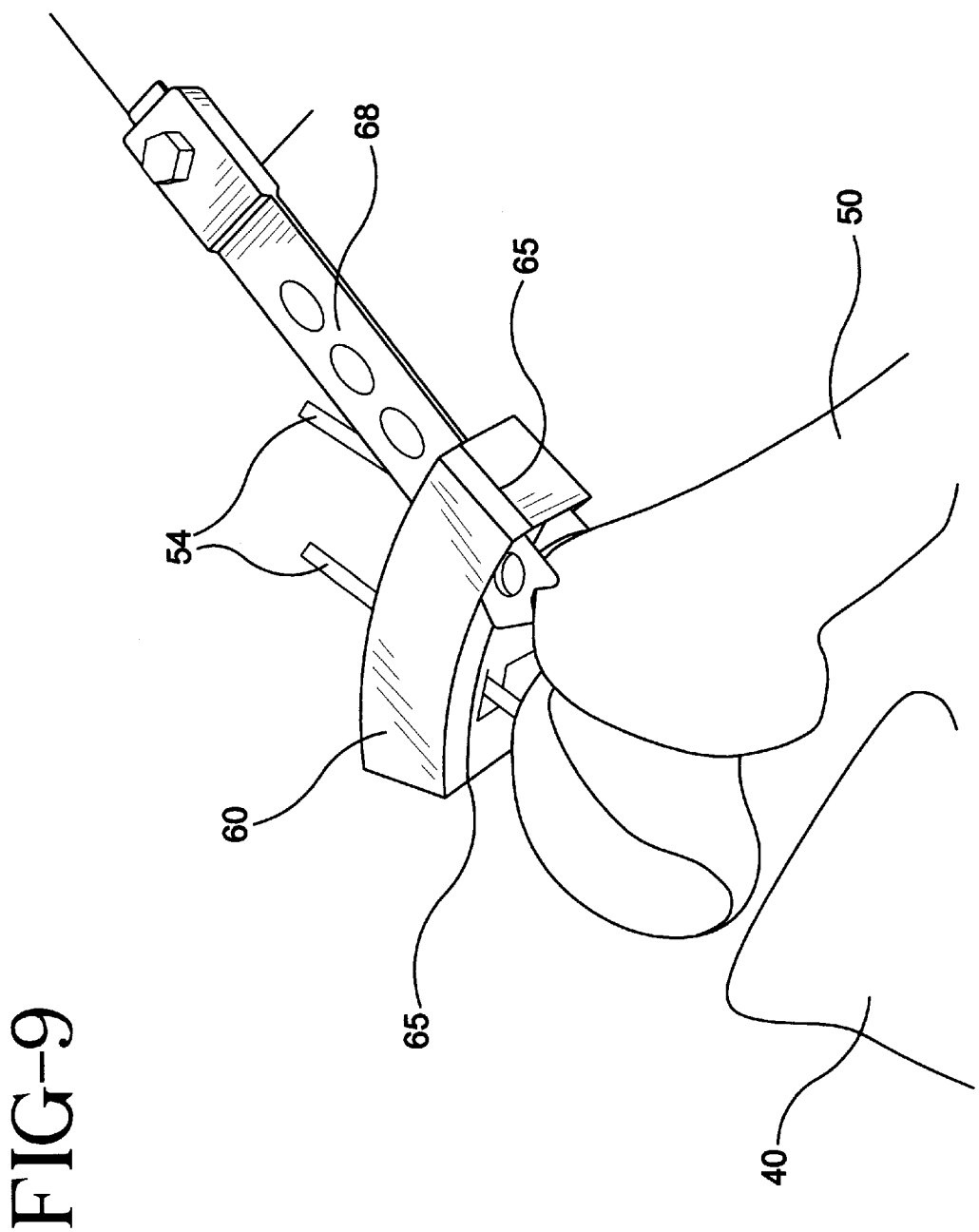
FIG. 9 shows the cutting guide in use.
Figure 11:
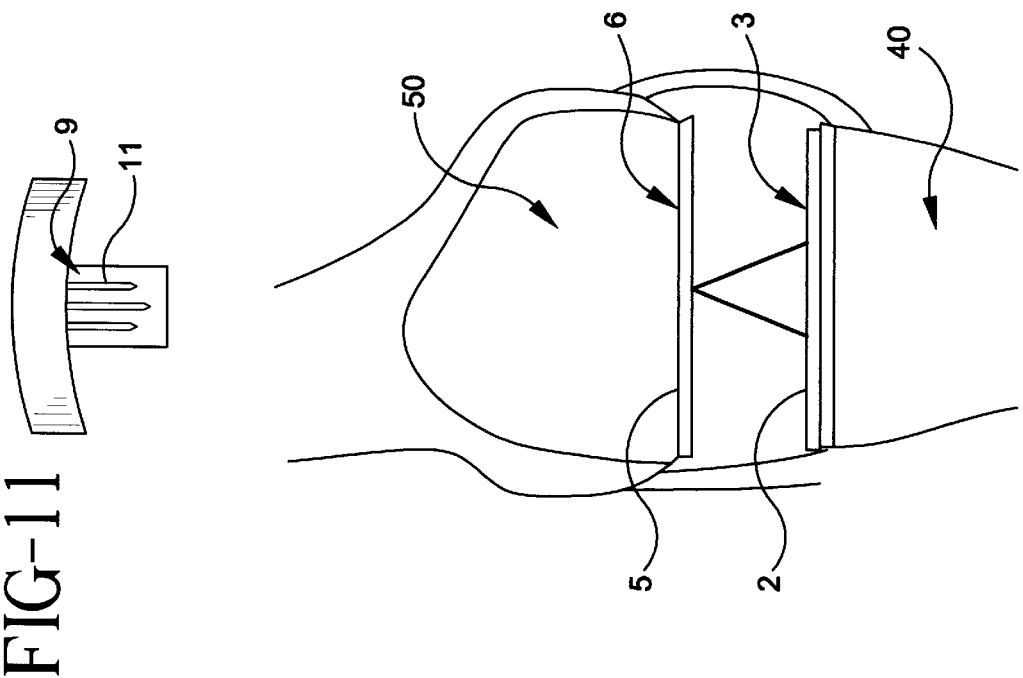
FIGS. 10 and 11 show how the apparatus can be used for ligament balancing.

As will be seen from FIG. 9, the cutting guide 60 is curved and when in position, a 0.9 mm saw blade 68 is used to now resection the distal femur. The distal resection guide 60 and pins 54 are then removed.

Figure 10:
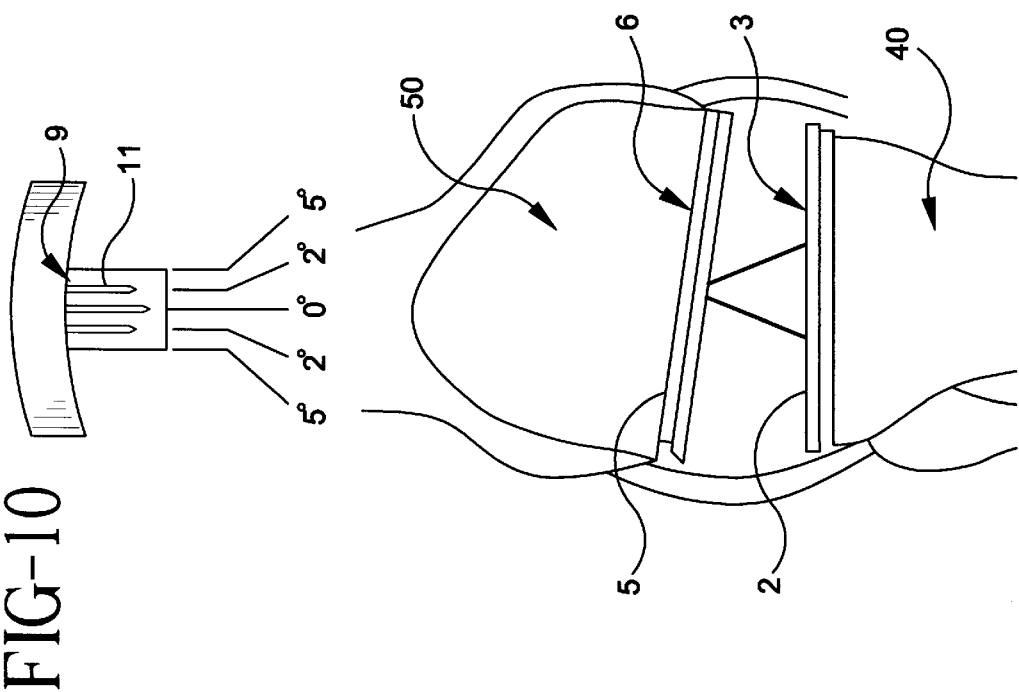

Ligament balancing extension is now carried out. In order to do this, the apparatus according to the invention is again used. The rotation latch operated by the tab 13 is released to allow free rotation of the second tissue engaging means 5. With the knee in extension, the jaws of the apparatus are inserted between the bones and are distracted to an appropriate tension. This position is shown in FIG. 10. In order to achieve a set torque, the key 17 can be removed from the shaft 16 and replaced by an appropriate breakaway torque wrench. When this is operated, it acts to limit the amount of load placed on the ligaments during this part of the procedure.

The tension can be relieved by releasing the ratchet lever 18.

If as shown in FIG. 10, there is imbalance in the joint, this can be read from the scale 11 on the plate 10. If the lateral and medial ligaments are imbalanced, appropriate soft tissue release is carried out until adequate balancing in achieved as shown in FIG. 1. Correct balancing is indicated on the scale 11.

When adequate balancing has been achieved, the drill guides 27 are reset by pressing the drill guide reset button 30 and pushing the drill guides right down onto the head 4 until the pins 32 engage in the recesses 31.

For ligament tensing the knee is again tensed in extension to the appropriate tension by use of the breakaway torque wrench and this action will raise and position the drill guides 27 for peg drilling in flexion, this position is shown in FIG. 12. It is important to be aware during this operation that a similar level of tension is to be reproduced when the knee is in flexion. This level must be sufficient to tense the ligaments in flexion.

To aid the assessment of this tension, the ratchet lever 18 is released, allowing the key or breakaway torque wrench to run quietly, smoothly and freely. Having reached the appropriate tension, the ratchet lock 18 is re-engaged and the surgeon must ensure that the drill guides 27 are pushed down so that the indentations 31 engage with the pins 32 carried on the moving head 4.

The breakaway torque wrench can be used again to limit the amount of load placed on the ligaments during this part of the procedure.

The drill guides are now set for the peg drilling operation in flexion and care must be taken not to resent the drill guides.

Ligament balance in flexion is achieved by setting the rotation lock to allow 5° rotation. With the knee in 90° flexion, the apparatus is again inserted as shown in FIG. 13 and the jaws are distracted to s similar tension to that used in the previous extension position, as shown in FIG. 12.

Figure 13:
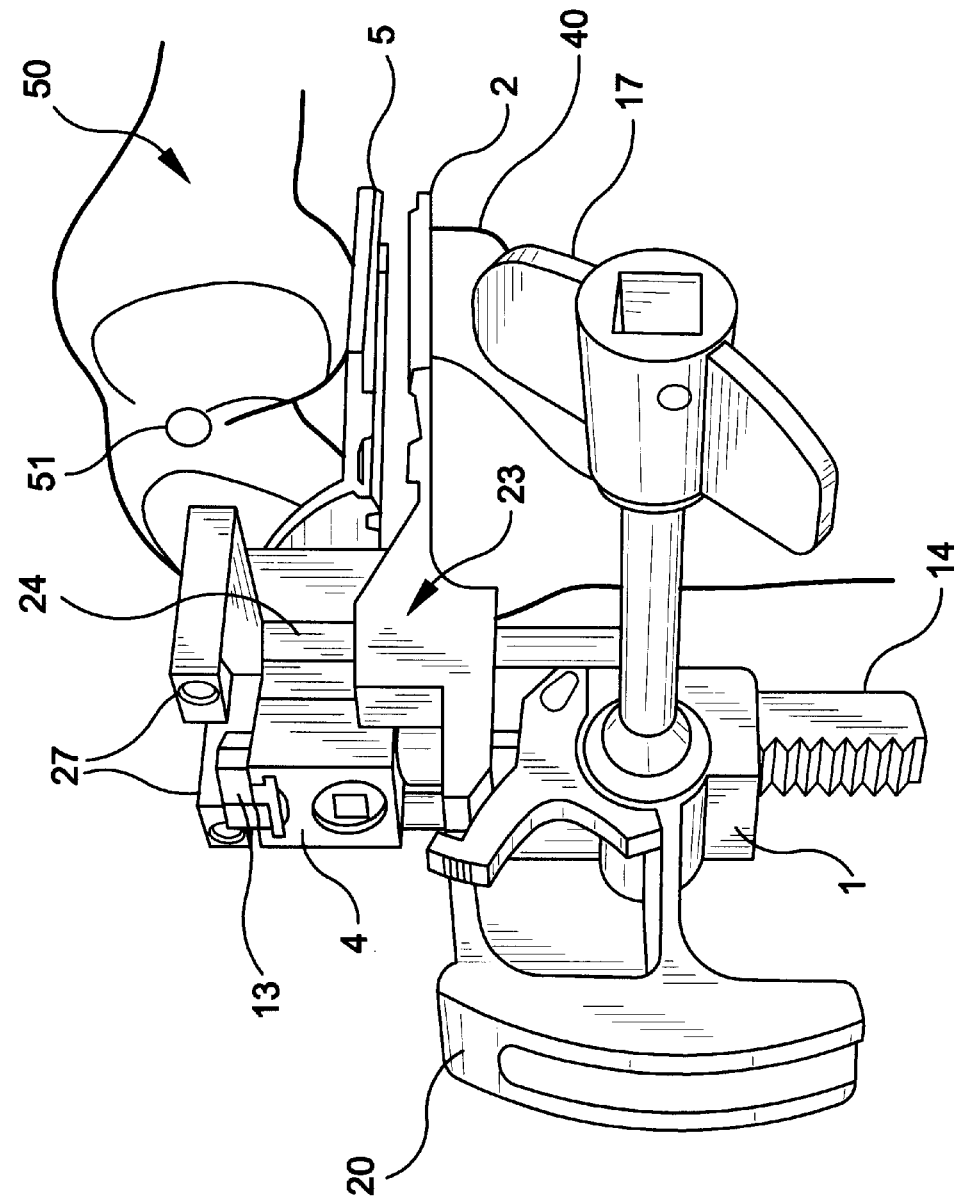
FIG. 13 shows the apparatus being used for ligament balance flexion.

As in extension, the breakaway torque wrench is again used to limit the amount of load placed on the ligaments during this part of the procedure, although, in FIG. 13, they key 17 is shown in position.

Figure 14:
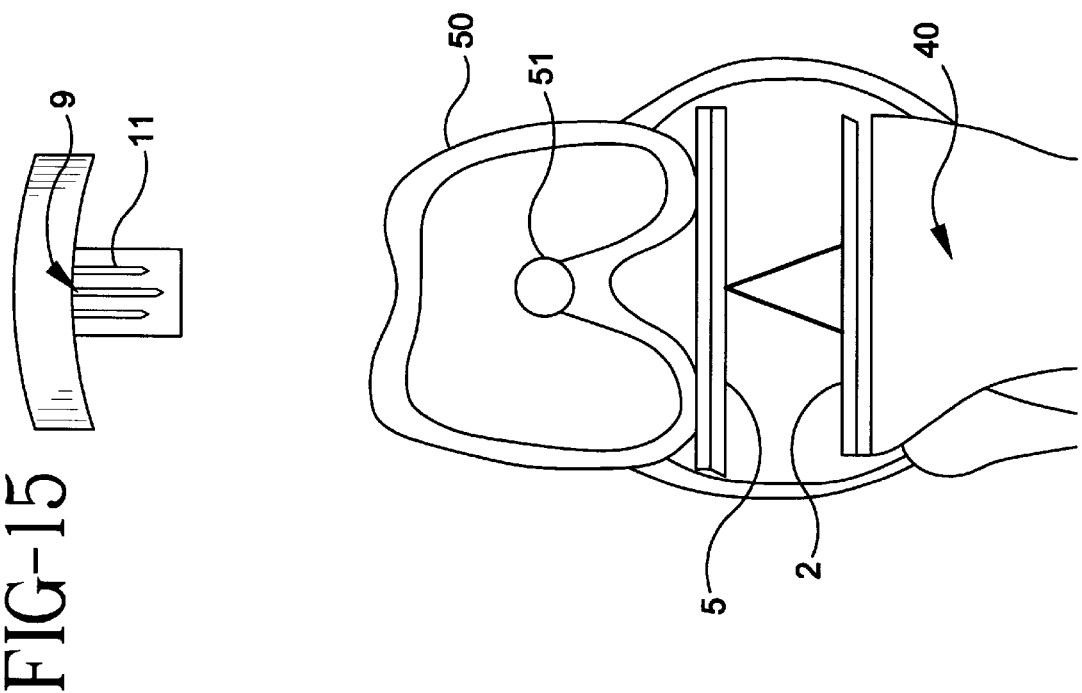
FIGS. 14 and 15 show the apparatus being used for ligament balancing in flexion.

Imbalance can be read from the scale 11 on the head 4 and if the lateral and medial ligaments are imbalanced, as shown in FIG. 14, the appropriate soft tissue release operation is again carried out.

Figure 15:
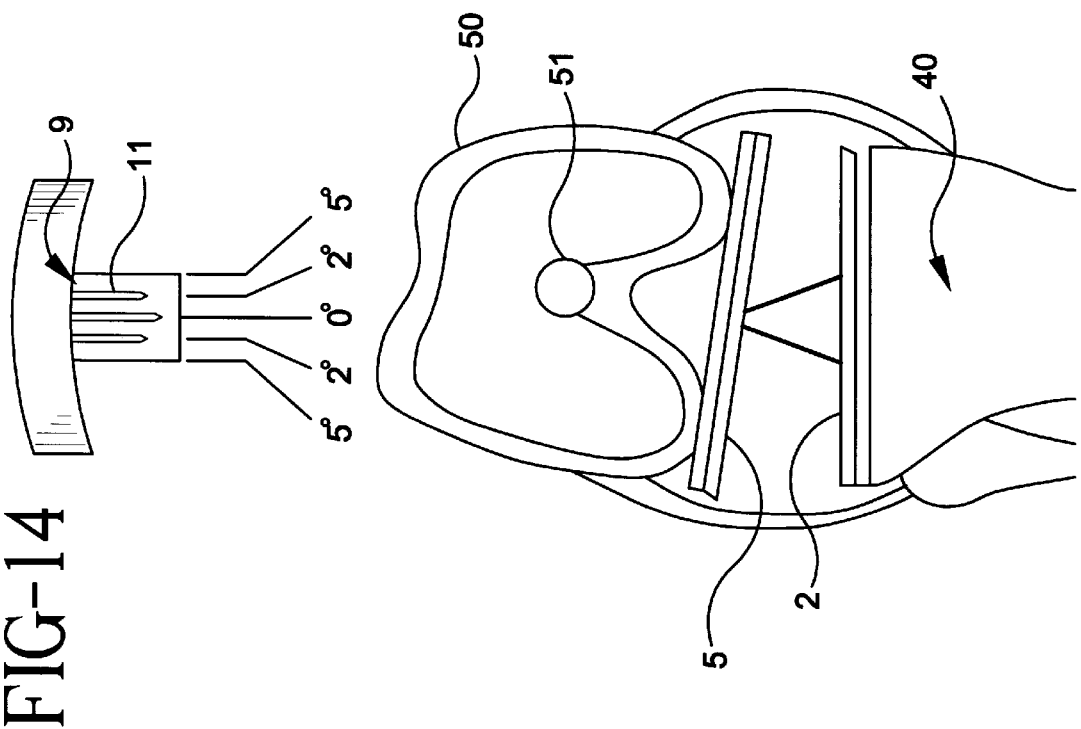

The correction of a significant flexion imbalance will affect the gap size between the proximal cut tibia 40 and the distal cut femur 50 in extension. If this correction is necessary it is essential to repeat the step of resetting the height of the drill guides and tensioning the knee in extension before proceeding to drill the peg drill holes in flexion. The balanced joint is shown in FIG. 15.

Figure 16:
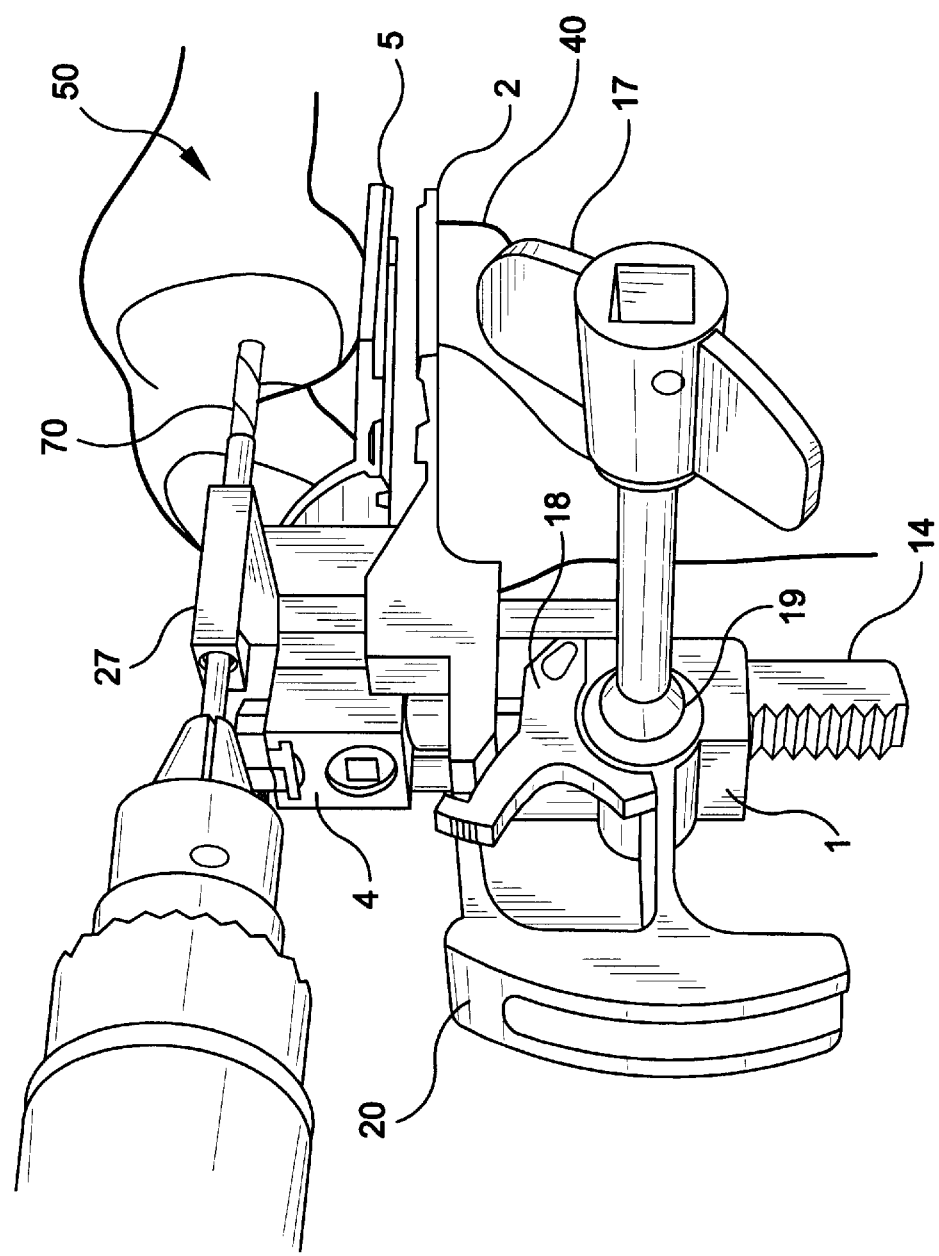
FIG. 16 shows the apparatus being set up for use in anterior and posterior femur, and anterior and posterior chamfer resection as shown in FIG. 2.

Anterior and posterior femur and anterior and posterior chamfer resection is carried out as follows. When preparing to peg drill, as shown in FIG. 16, it is essential to ensure that the knee is held in position at 90° flexion. This will help ensure the femoral cutting guide is correctly positioned in the A-P plane on the cut distal face.

A visual check can be made using the 90° angle on the I-M rod as a guide.

Maintaining the correct tension (the same as or slightly less than the tension set in extension) the peg holes are drilled with a 3.2 mm drill, indicated by reference numeral 70 in FIG. 16, by drilling through the drill guides 27, the drill bits again acting as location means for the cutting guide.

The size of the femoral component is based upon achieving the correct anterior cut and the desire to restore and maintain a balance patello-femoral articulation.

Figure 17:
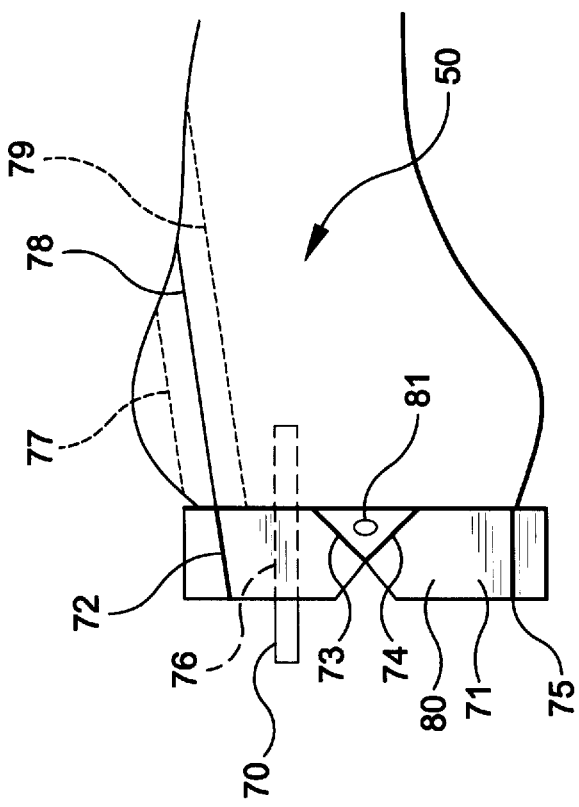
FIG. 17 is a diagrammatic illustration showing how the resection can take place using a cutting guide.
Figure 18:
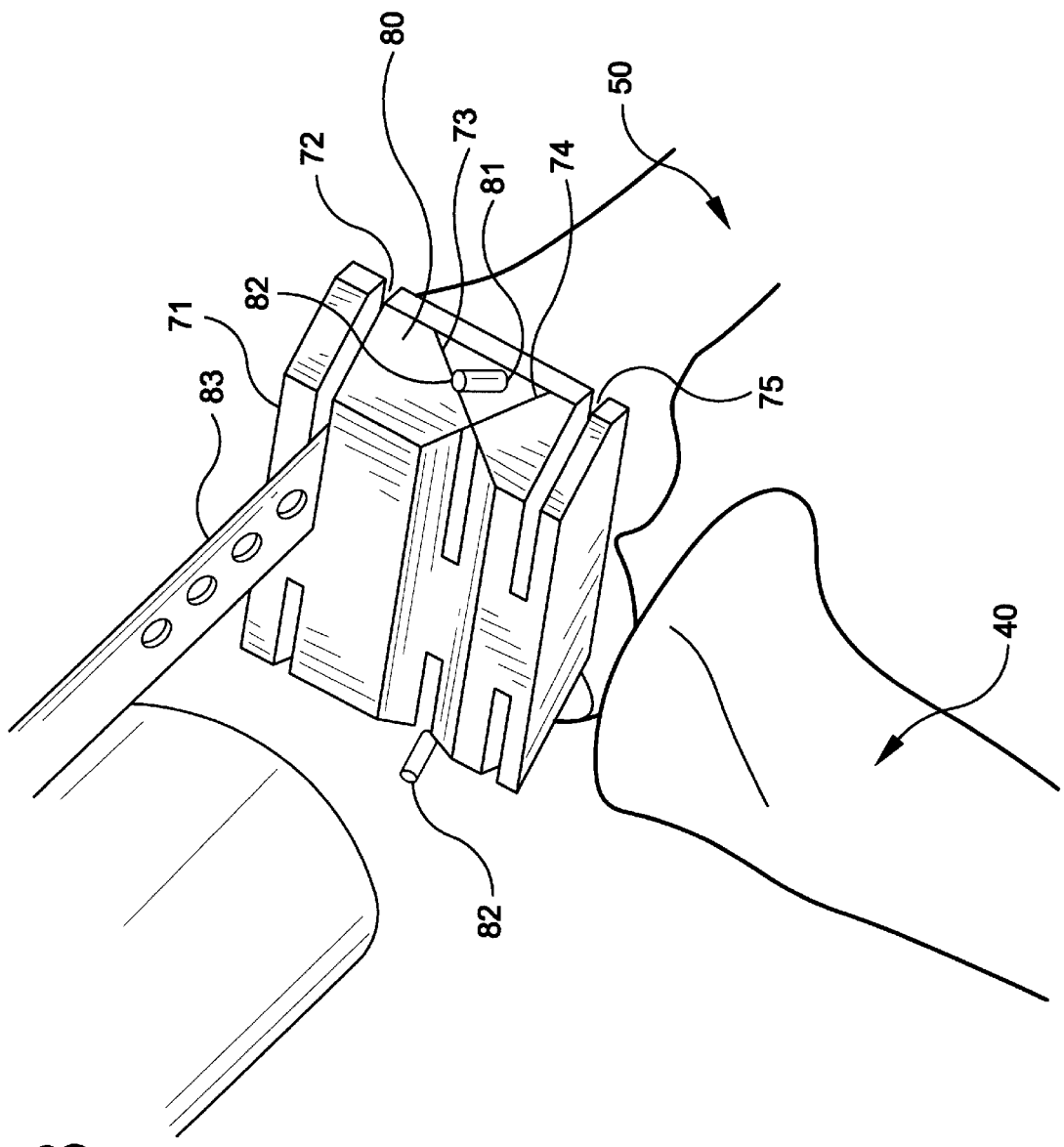
FIG. 18 shows how a cutting guide is used.

A cutting guide suitable for this operation is shown in FIGS. 17 and 18 and comprises a body portion 71 provided with pairs of alternative cutting slots 72, 73, 74 and 75. In order to clarify the drawing the openings to receive the drill pins 70 and the drill pins 70 themselves are omitted in FIG. 18. Alternative pairs of openings are provided to accommodate the alternative cutting slots 72, 73, 74 and 75. The different cuts are indicated in FIG. 17 by reference numerals 77, 78 and 79 but only one pair of openings 76 are shown in FIG. 17. The body portion 71 has angled sides 80 and additional openings 81 to receive further drills or fixing pins 82 to further secure the cutting guide in place.

Figure 19:
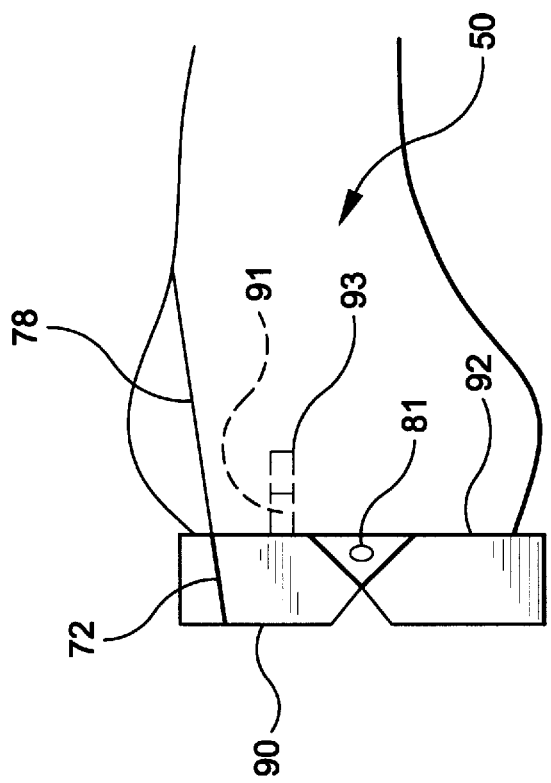
FIG. 19 is a view similar to FIG. 17 showing the use of an alternate construction.

The anterior cut 78 can be anticipated by inserting a femoral sizing indicator or a 0.9 mm saw blade 83 through the side of an anterior slot 72 on the cutting guide or femoral sizing guide as shown in FIGS. 18 and 19. The appropriate size of the cutting guide is selected.

Once the correct size of cutting guide has been chosen, it is assembled into the drill 70 by engaging openings 76, drills 82 can be added through the holes 81 on the side of the guide for secure fixation as shown in FIG. 17.

When the cutting guide is secure, femoral cuts are made with an oscillating saw and saw blade as shown in FIG. 18 using saw cutting slots, for example 72.

The femoral and tibial preparation can then be continued in known manner for the acceptance of the prosthesis.

As described above, drill bits are used as first location means for the cutting guides, but alternatively, the drill guides can be formed to accept screws, nails, rods or pins which can act as location elements.

In the construction of the apparatus as described above and as shown in FIGS. 1 to 18, the first location means to locate the cutting guide are in the form of elongate elements which cooperate with second location means on the cutting guide which are in the form of openings. In an alternative construction, however, the first location means can be provided by an opening in the bone and the second location means can be provided on the cutting guide by an abutment which is dimensioned to locate in the opening in the bone.

Thus, the same apparatus can be used for tensing and providing the guide means as described in the preceding figures but it is used in a different way. The cutting guide, however, is of different construction. An appropriate cutting guide is shown in FIG. 19 and in which the same reference numerals are used to indicate the same parts as the cutting guide shown in FIGS. 17 and 18. In this construction however, the cutting guide 90 is provided with a pair of abutments 91 which project from its rear face 92. The abutments 91 are dimensioned and spaced to located in drilled openings 93 in the bone 50.

With this arrangement therefore the operating technique is the same as that described with regard to FIGS. 1 to 18 but when drills 54 and 80 are used to drill into the bone, they are not left in place to act as the first location means, but are removed. The holes 91 provided by the drills, and as shown in FIG. 19, act as the first location means themselves, the second location means being provided by the abutments 91 on the cutting guide 90.

I claim:

1. A knee tensioning appratus comprising:
    a base, a first and second tissue engaging elements mounted on said base and being displaceable towards and away from each other, the first of said tissue engaging elements being adapted to be oriented by the tissue engaged thereby;
    a guide element adjustable in relation to said base and a second of said tissue engaging elements for positioning a first location element to locate a cutting guide provided with a cooperating second location element on a bone to be resectioned;

said guide element being carried by said second tissue engaging element and arranged to move in relation to the base in accordance with movement of the second tissue engaging element;

said guide element is carried by a releasable rachet locking element movably located on the base and can be moved in only one direction by the second tissue engaging element;

said first tissue engaging element being located in a fixed relationship to the base and said second tissue engaging element comprising a movable head carrying a tissue engaging element provided with a tissue engaging surface and said guide element being moved by movement of said movable head;

said guide element engaging the movable head and is carried on a support movably mounted on the base; and said second tissue engaging element being rotatable and having a lock for locking said second tissue engaging element in two or more angular positions.

2. The apparatus as claimed in claim 1 in which said guide element includes a guide bore.

3. The apparatus as claimed in claim 2 in which said guide bore is dimensioned to receive said first location element in the form of an elongated medullary guide to be inserted into a canal of said bone.

4. The apparatus as claimed in claim 3 in which said elongate guide is a drill, screw, or rod.

5. The apparatus as claimed in claim 3 in which a second location element is provided by a location opening in said cutting guide.

6. The apparatus as claimed in claim 5 in which said first location element is an opening in said bone formed by an elongate forming means guided through said guide bore.

7. The apparatus as claimed in claim 6 in which said second location element is provided by an abutment on said cutting guide which is dimensioned to locate in said opening in said bone.

8. The apparatus as claimed in claim 7 in which said cutting guide is provided with additional bores to receive attachment elements to further locate it on said bone.

9. The apparatus as claimed in claim 1 in which the tissue engaging elements each include a tissue engaging surface, each of said tissue engaging surfaces being arranged so that it faces away from the other.

10. The apparatus as claimed in claim 1 in which two guide elements are included and are arranged in spaced apart relationship in relation to one of said tissue engaging elements.

11. The apparatus as claimed in claim 1 in which the second tissue engaging element is adapted to be rotationally oriented by the tissue engaged thereby with respect to the long axis of said bone.

12. The apparatus as claimed in claim 1 in which said tissue engaging element is carried by a rotatable shaft mounted in said movable head.

13. The apparatus as claimed in claim 1 further including measuring means to measure the degree of rotary deflection of said second tissue engaging surface away from a position of parallelism with the first tissue engaging surface when first and second tissue engaging surfaces engage the tissue.

14. The apparatus as claimed in claim 13 further including a drive mechanism to displace the tissue engaging elements away from each other and which mechanism includes a geared drive.

15. The apparatus as claimed in claim 14 in which said geared drive mechanism includes a rack and pinion assembly.

* * * * *

UNITED STATES PATENT AND TRADEMARK OFFICE
CERTIFICATE OF CORRECTION

PATENT NO. : 5,911,723
DATED : June 15, 1999
INVENTOR(S) : Ashby et al.

It is certified that error appears in the above-identified patent and that said Letters Patent is hereby corrected as shown below:

On the title page item [73],

"Howmedice" should read -- Howmedica --.

Signed and Sealed this

Nineteenth Day of December, 2000

Attest:

Q. TODD DICKINSON

*Attesting Officer*     *Commissioner of Patents and Trademarks*